(12) United States Patent
Flohr et al.

(10) Patent No.: US 7,695,193 B2
(45) Date of Patent: Apr. 13, 2010

(54) X-RAY SYSTEM FOR THE CREATION OF DIAGNOSTIC X-RAY IMAGES USING CONTRAST MEDIA

(75) Inventors: Thomas Flohr, Uehlfeld (DE); Michael Grasruck, Erlangen (DE); Hubertus Pietsch, Kleinmachnow (DE); Karl Stierstorfer, Erlangen (DE); Christoph Suss, Erlangen (DE); Hanns-Joachim Weinmann, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 45 days.

(21) Appl. No.: 12/084,259

(22) PCT Filed: Oct. 25, 2006

(86) PCT No.: PCT/EP2006/067741

§ 371 (c)(1),
(2), (4) Date: Jul. 29, 2008

(87) PCT Pub. No.: WO2007/051739

PCT Pub. Date: May 10, 2007

(65) Prior Publication Data

US 2008/0310582 A1    Dec. 18, 2008

(30) Foreign Application Priority Data

Oct. 31, 2005   (DE) .................. 10 2005 052 368

(51) Int. Cl.
*G01D 18/00* (2006.01)
(52) U.S. Cl. .................... 378/207; 600/431

(58) Field of Classification Search ............... 378/4–20, 378/62, 98.11, 98.12, 207; 600/407, 420, 600/425, 427, 431, 436
See application file for complete search history.

(56) References Cited

U.S. PATENT DOCUMENTS 3,848,130 A    11/1974  Macovski
(Continued)

FOREIGN PATENT DOCUMENTS

DE    28 27 146    1/1979
(Continued)

OTHER PUBLICATIONS

Fobbe et al.: "Arterial Angiography in High-Kilovoltage Technique with Gadolinium as the Contrast Agent: First Clinical Experience", Eur. Radiol. 1996, vol. 6, pp. 224-229, Others.
(Continued)

*Primary Examiner*—Courtney Thomas
(74) *Attorney, Agent, or Firm*—Harness, Dickey & Pierce, P.L.C.

(57) ABSTRACT

An x-ray system is disclosed including a selector for finding an optimum combination between the contrast medium and the energy spectrum of an x-radiation for a scan to optimize the noise-to-contrast ratio. A method for creating X-ray images is also provided. The x-ray images are created with the aid of contrast media by taking into account an optimal combination between the contrast medium and the energy spectrum of an X-radiation used for a scan. A method for the use of a lanthanide-containing complex to produce a contrast medium for optimizing the combination between the contrast medium and the radiation to obtain a maximum contrast-to-noise ratio in an X-ray image is also provided.

45 Claims, 7 Drawing Sheets

U.S. PATENT DOCUMENTS

| | | |
|---|---|---|
| 4,160,906 A | 7/1979 | Daniels et al. |
| 5,687,208 A | 11/1997 | Bae et al. |
| 2002/0071521 A1 | 6/2002 | Ohishi |
| 2005/0053551 A1 | 3/2005 | Badiola |
| 2005/0084060 A1 | 4/2005 | Seppi et al. |
| 2005/0123093 A1 | 6/2005 | Lawaczeck et al. |
| 2006/0224066 A1 | 10/2006 | Niethammer |
| 2007/0160180 A1 | 7/2007 | Maschke |

FOREIGN PATENT DOCUMENTS

| | | |
|---|---|---|
| DE | WO 2005/034755 | 4/2005 |
| DE | 10 347 961 | 6/2005 |
| DE | WO 2005/070294 | 8/2005 |
| DE | WO 2005/072614 | 8/2005 |

OTHER PUBLICATIONS

Schmitz et al.: "Evaluation of Gadobutrol in a Rabbit Model as a New Lanthanide Contrast Agent for Computed Tomography", Investigative Radiology, 1995, vol. 30, No. 11, pp. 644-649, Others.

Kalinowski et al: "1-Molar Gadobutrol as a Contrast Agent for Computed Tomography: Results From a Comparative Porcine Study", Investigative Radiology, 2003, vol. 38, No. 4, pp. 193-199, Others.

Quinn et al.: "Gd-DTPA: An Alternative Contrast Medium for CT", Journal of Computer Assisted Tomography, 1994, vol. 18, No. 4, pp. 634-636, Others.

German Office Action issued Aug. 11, 2006.

FIG 5 Mass ratio with the same $CNR^2$/dose
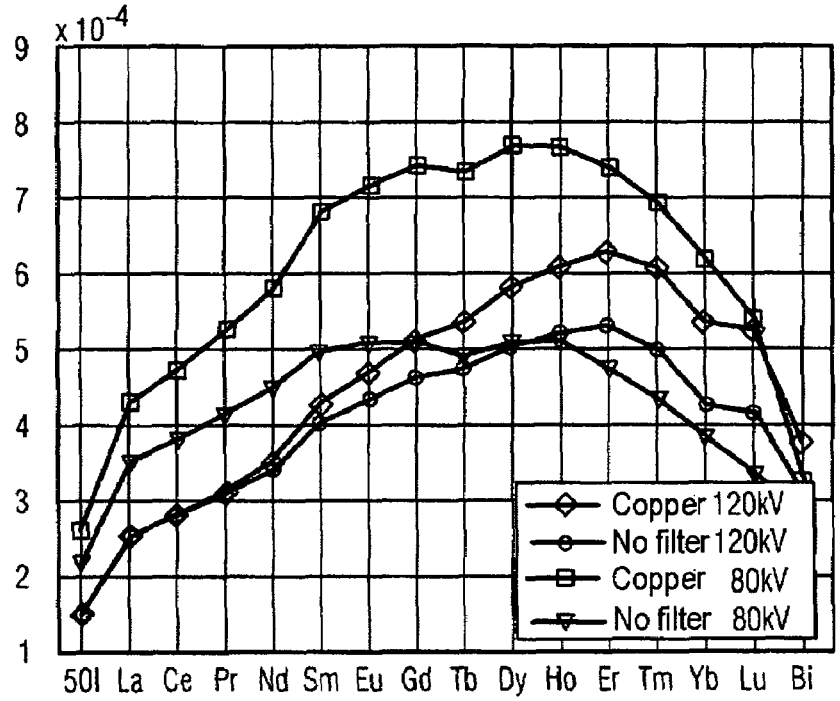
FIG 6 Mass ratio with the same $CNR^2$/dose
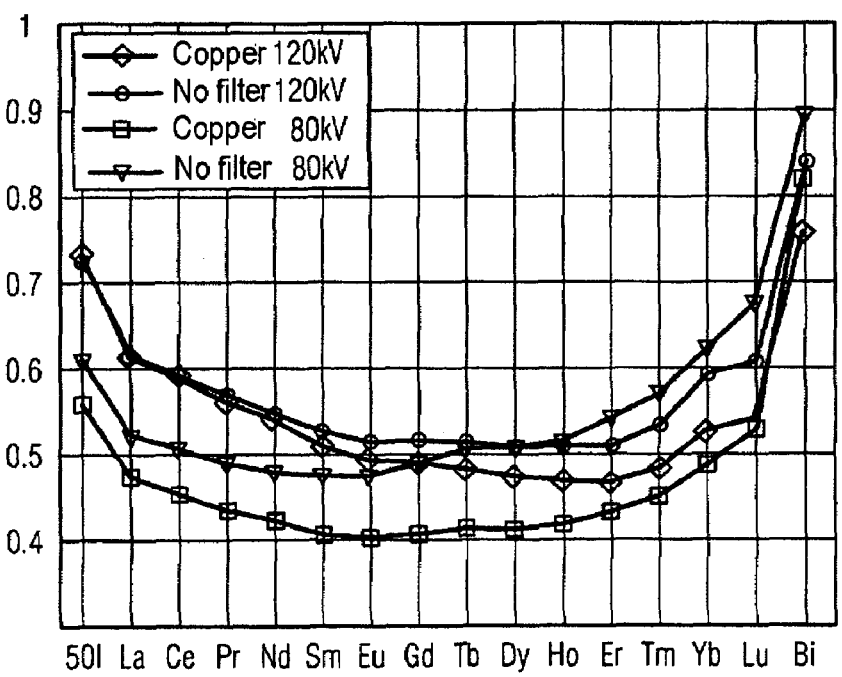

US 7,695,193 B2

X-RAY SYSTEM FOR THE CREATION OF DIAGNOSTIC X-RAY IMAGES USING CONTRAST MEDIA

PRIORITY STATEMENT

This application is the national phase under 35 U.S.C. §371 of PCT International Application No. PCT/EP2006/067741 which has an International filing date of Oct. 25, 2006, which designated the United States of America, and which claims priority on German Patent Application number 10 2005 052 368.4 filed Oct. 31, 2005, the entire contents of each of which are hereby incorporated herein by reference.

FIELD

At least one embodiment relates to an X-ray system for creating diagnostic X-ray representations of a patient. The X-ray system includes an X-ray tube, a detector, a contrast medium application unit and a control and computation unit. The X-ray system is capable of selecting different operating parameters, at least with respect to the energy spectrum used for the X-ray radiation.

At least one other embodiment relates to a method for optimization of tomographic representations of a patient using X-ray beams with a selectable energy spectrum, and measurement of the attenuation of the X-ray radiation passing through the patient at different spatial angles and with contrast medium additionally being given in order to improve the contrast in the tomographic representation.

In addition, at least one embodiment relates to the use of a complex containing lanthanoid for production of a contrast medium for diagnosis assistance in an X-ray examination.

BACKGROUND

The aim of X-ray computed tomography is to represent the internal structure of a living body, generally for diagnostic purposes, by non-invasive examinations. Since the absorption behaviors of these structures differ only slightly, contrast medium is frequently applied to produce a high-contrast representation. The contrast medium either accumulates on specific body structures, such as carcinomas, or enriches specific body fluids, for example blood. Contrast mediums such as these generally contain elements that are distinguished by a high absorption coefficient, and therefore, provide good contrast from the surrounding tissue, with a relatively low absorption coefficient.

Conventional practice in this context is to use contrast mediums containing iodine. Contrast mediums containing gadolinium are also used because of the possibility of the patient being examined not being compatible with iodine. In this context, contrast mediums containing lanthanoid are also generally proposed. In this context reference should be made, for example, to the documents "Arterial angiography in high-kilovoltage technique with gadolinium as the contrast medium: first clinical experience", F. Fobbe et al., Eur. Radiol. 6, 224-229 (1996), Springer-Verlag; "Evaluation of Gadobutrol in a Rabbit Model as a New Lanthanide Contrast medium for Computer Tomography", Stephan A. Schmitz et al., Investigative Radiology, Vol. 30, No. 11, 644-649 (1995), Lippincott-Raven Publishers; "1-Molar Gadobutrol as a Contrast medium for Computed Tomography: Results from a Comparative Procine Study", Marc Kalinowski et al., Investigative Radiology, Vol. 38, No. 4, 193-199 (2003), Lippincott Williams & Wilkins, Inc. and "Gd-DTPA: An Alternative Medium for CT" Aidan D. Quinn et al., Journal of Computer Assisted Tomography, 18(4): 634-636 (1994) Raven Press Ltd.

These documents also describe examinations which indicate the absorption of a number of specific contrast mediums in Hounsfield units. The examinations are also based on different X-ray spectra. However, these examinations provide the operator only with the knowledge that a contrast medium with a higher atomic number leads to better imaging results with the radiation that is being used. In addition, the known effect of the linear relationship between the concentration of the contrast medium and the measured absorption is described. No direct aid is provided for selection of an optimum combination of contrast medium to the X-ray spectrum for specific examination areas of a patient, and for achieving an optimum contrast-to-noise ratio.

SUMMARY

At least one embodiment provides an X-ray system and a method for optimization of X-ray representations, which allows an operator to use relatively simple means—which can be coped with in practice—to select the optimum combination for a specific examination of the contrast medium and X-ray spectrum being used in order to achieve the best possible contrast-to-noise ratio in an X-ray representation.

According to at least one embodiment, the inventors have discovered that it is not sufficient just to select a contrast medium having an element with as high an atomic number as possible to achieve an optimum contrast-to-noise ratio. In fact, depending on the respective area of the patient being examined, an optimum combination between the contrast medium and the energy spectrum of the X-ray radiation being used for the examination is required. The relationships between the absorption and the energy spectrum of the radiation taking into account an optimum contrast-to-noise ratio for the respectively predetermined or given examination area of a patient are in this case relatively complex and cannot be defined by simple rules or formulae. More particularly, for example, a change in the thickness of the examination volumes also leads to a shift in the maxima considered for the optimum contrast-to-noise ratios.

Trials or simulations may be carried out by means of which the contrast-to-noise ratio is represented as a function of the radiation spectrum used, the respective contrast medium and the path length of the transilluminated examination volume, referred to for simplicity in the following text as the "examination volume".

Furthermore, the surrounding tissue area for examination can also be included in these parameters. Different surrounding tissue areas such as bone, the heart, the liver or the brain, also result in differences in the selection of the optimum contrast medium/energy spectrum combination because of the different absorption behavior of the respective tissue.

The selection may not only relate to the various contrast-producing elements or different contrast mediums, but also be necessary to draw distinctions relating to the optimum chemical structure of the contrast medium. For example, a different molecule is used for a contrast medium intended only to provide enrichment in the blood circulation and to be dissipated later than for a contrast medium which is intended to accumulate in the form of a marker on carcinogenic structures. It is also possible to select combinations of the two variants to allow optimum identification in an X-ray representation.

The concentration of the contrast medium is also included as a variable in this list. To obtain comparable ratios for different contrast mediums, their application concentration may be used as a measure, or the compatibility of the respective contrast medium may be used. Appropriately normalized contrast medium concentrations can be used to compare different contrast mediums and to select the optimum contrast medium/radiation combination. An improved variant can also include a spectrum-dependent damage factor of the radiation because, in principle, it can be assumed that higher-energy X-ray radiation has a less damaging effect than low-energy X-ray radiation.

It should be noted also that the contrast-to-noise ratio can also be improved by increasing the dose. As is known, increasing the dose by a factor x results in the contrast-to-noise ratio being improved by the factor $\sqrt{x}$. However, the aim of all the efforts in the field of radiological examinations is to reduce and/or minimize the radiation dose used for an X-ray examination such as this. The optimization of the contrast-to-noise ratio therefore relates to the same radiation dose. In other words, the dose used—or the radiation load on the patient being examined—is minimized by optimum choice of a contrast medium which gives the best contrast-to-noise ratio, by presetting a specific contrast-to-noise ratio in the image.

On the one hand, the contrast-to-noise ratio can be achieved by increasing the concentration of a contrast medium. On the other hand, the patient should not be loaded with excessive contrast medium doses for compatibility reasons. Ideally, the combination of contrast medium and X-ray radiation should therefore be found which, normalized with respect to the radiation dose used, normalized with respect to its damaging effect and normalized with respect to the concentration of the contrast medium, or its compatibility, gives the best contrast-to-noise ratio, with the CT examination then being carried out with a minimized dose and contrast medium concentration on the basis of this determined contrast medium/radiation combination such that an image with sufficiently good contrast for clinical assessment can be reconstructed. A further exacerbating factor in this case is that the optimization also depends on the path length of the radiation through the patient and on the hardening of the radiation associated with this.

Since it is no longer possible for an operator of an X-ray system to overlook the complexity of these relationships particularly in everyday clinical use, it appears necessary to provide the operator with a selection means for an optimum X-ray examination. The selection means uses criteria, which can be defined relatively easily, to provide at least an optimum contrast medium/radiation combination or, if there are a plurality of equivalent contrast medium/radiation combinations, to offer them to the operator for final selection. When making this final selection from a plurality of equivalent contrast medium/radiation combinations the operator can take into account other aspects, for example individual compatibility with the patient, cost aspects or the like.

On the basis of these discoveries, the inventors propose that an X-ray system for the creation of diagnostic X-ray representations of a patient be improved, preferably an X-ray system having at least one X-ray tube for production of a beam composed of X-rays with an energy spectrum for scanning the patient, a detector for measurement of the attenuation of the X-ray radiation as it passes through the patient, an application unit for providing contrast medium to improve the contrast in the tomographic representation of the patient, a control and computation unit for controlling the X-ray system and for creation of the X-ray representations of the patient with the aid of stored and executed computer programs. The X-ray system is capable to select different operating parameters at least with respect to the energy spectrum of the X-ray radiation used. The X-ray system includes a selection means which, after direct or indirect statement of the parameters, presets at least one combination of contrast medium and energy spectrum of the X-ray radiation for the examination, by means of which an optimum contrast-to-noise ratio is achieved in the examination area with the radiation dose and contrast medium load being very low. The parameters include the examination volume on the one hand and the examined tissue structure on the other hand.

In at least this embodiment, the selection means is itself generally formed by computer programs in conjunction with an input keyboard and a display unit. In principle, however, it is also within the scope of the present invention to provide specific keys, possibly associated with specific displays, on the X-ray system. The operator is provided with a suitable means to allow him to pass on the necessary presets to the system.

This selection means allows the operator to find the optimum combination of contrast medium and energy spectrum to be used simply by stating or selecting a body region to be examined or the tissue structure to be examined. For example, this can be done by the selection means having a look-up table in which optimum combinations of contrast medium and the energy spectrum of the X-ray radiation to be used are stored as a function of the body region to be examined or the tissue structure to be examined.

In addition, the selection means can be connected to the control system of the X-ray system so that the operator selection, provided that he makes a clear choice of optimum contrast medium and energy spectrum, automatically leads to appropriate setting of the X-ray system with respect to the tube voltage used and/or a filter to be used for the radiation. If a plurality of equivalent solutions are available, these can be offered to the operator for further selection.

It may also be advantageous to operate the detector in different operating modes, specifically as an integrating detector, event-counting detector or energy-specific detector, in which case the optimum choice can also be given or predetermined by the selection means. This is because the optimum choice of the contrast medium/energy spectrum combination may also be influenced by different operating modes of the detector.

If an energy-selective detector having at least two energy ranges which can be counted separately is used then both integrating detection and event-counting detection can be carried out in these energy ranges. At least one limit value between the detected energy ranges is variable. In this case, the selection means may be connected to a control system for this limit value and optimally may preset this limit value appropriately in order to achieve the best contrast-to-noise ratio.

In addition to being capable of defining the examination volume or the examination cross section by inputting a diameter with an approximately circular cross section or two axis lengths with an approximately ellipsoid cross section, the inventors also propose that an indirect input capability for the examination volume be provided in the X-ray system, by indication of the body region. For example, a very good approximation to these values can be obtained just by stating the examination regions as the head, thorax, or abdomen.

Further options are to define the recording of a topogram, an optical definition or the examination volume by a weight determination, preferably by means of a weighing apparatus in the patient couch. However, combinations of these measures may also be used in order to achieve better results.

It is also particularly advantageous to define the examination volume by a prescan and to transfer this into the system, preferably automatically. This method allows the actual cross section of the examination volume to be defined without any further approximations, so that no approximation errors occur.

According to embodiments of the present invention, the proposed X-ray system may be a system for creation of transmission images and also an X-ray system for creation of tomographic representations, that is to say a CT system or a C-arc appliance with means for reconstruction of tomographic images, with a preferred application being for tomographic systems. In the case of an X-ray system such as this for creating tomographic representations, the X-ray tube or tubes and, if appropriate, the detector or detectors are also mounted such that it (or they) can rotate around the patient thus making it possible to record a multiplicity of projections from different projection directions. Furthermore, means are provided for data preprocessing, in particular for reconstruction of CT representations, with these means generally comprising a combination of a computation unit and appropriate computer programs.

The contrast-to-noise ratio also can advantageously be optimized by providing contrast medium which has at least one contrast medium complex and contains as the contrast material a choice of at least two contrast-producing elements from the following list: I, La, Ce, Pr, Nd, Sm, Eu, Gd, Tb, Dy, Ho, Er, Tm, Yb, Lu, Bi. In one embodiment, the at least two contrast-producing elements are selected from Dy, Ho, Er, Tm, Yb or Lu.

In accordance with embodiments of the present invention, the inventors propose a method for optimizing tomographic representations of a patient by means of X-ray beams having an energy spectrum which can be selected, and measurement of the attenuation of the X-ray radiation as it passes through the patient at different spatial angles, with contrast medium additionally being given to improve the contrast in the tomographic representation, in which before the examination, the contrast-to-noise ratio of different energy spectra of the X-ray radiation and different contrast mediums relative to tissue or to material similar to tissue is determined for the CT system, and before the examination of a patient by the X-ray system, an optimized selection of at least one contrast medium/X-ray spectrum combination is provided on the basis of a given or predetermined examination area of the patient and allows an optimum contrast-to-noise ratio in the examination area.

According to embodiments of the present invention, a look-up table can be used for selection, in which at least one optimum combination of contrast medium to energy spectrum of the X-ray radiation to be used is stored as a function of the predetermined examination area of the patient.

Alternatively, after a prescan of the examination area, possibly using different energy spectra, the optimum combination of contrast medium and energy spectrum of the X-ray radiation used for scanning can be determined on the basis of the actual absorption values in the examination area by simulation using different available contrast mediums and energy spectra, possibly also detectors or detector operating modes.

According to a further embodiment, once the selection of the contrast medium has been initiated by the operator, the tube voltage can also be set automatically and/or the energy spectrum of the X-ray radiation used can be set automatically by filtering in accordance with the previously stored or calculated details. Radiation events can be counted or the radiation arriving at the detector can be detected on an energy-specific basis to determine the absorption of the radiation in the detector.

In the case of energy-specific detection, at least two energy ranges may be detected separately, but in an integrating manner depending on the energy range, with the at least one limit value between the detected energy ranges being variably adjustable, and with this limit value being controlled as a function of the selection made by the operator and existing presets as a function of the contrast medium used and the energy spectrum of the X-ray radiation.

Alternatively, at least two energy ranges can also be detected separately, and on an event-counting basis, with the at least one limit value between the detected energy ranges being variably adjustable, and with this limit value being controlled in accordance with the selection made by the operator and existing presets as a function of the contrast medium used and the energy spectrum of the X-ray radiation.

In one particular embodiment a measure of the patient volume, such as the cross section of the patient to be examined through which the radiation has to pass, can be entered directly or indirectly to select the optimum combination of contrast medium and energy spectrum. If entered indirectly it is possible, for example, to use a look-up table which deduces the actual patient volume and/or the cross section to be penetrated from other details.

By way of example, the patient volume can be determined by recording a topogram and the geometric data which can be derived from it, and can be transferred to the X-ray system, preferably automatically. The patient volume also can be determined optically, in a corresponding manner. Furthermore, alternatively or in addition to the indirect determination processes mentioned above, the weight of the patient can also be determined, preferably by means of a weighing apparatus in the patient couch, so that a generally additional parameter is available for estimation of the patient cross section in the examination area.

A prescan can be used as a particularly exact method for determination of the patient volume, in which case it is also possible at the same time in this way to define the approximate absorption without contrast mediums, in order to use this data and simulation calculations with contrast medium to predetermine the optimum combination of contrast medium to be used and energy spectrum even better, and to transfer this, possibly automatically, to the X-ray system with the X-ray system being configured appropriately.

The method can be used analogously to the X-ray system described above, both for production and representation of transmission records and for representation of tomographic records, by means of appropriate reconstruction steps which are known per se.

According to embodiments and with regard to the available contrast mediums, it is also possible to select at least two contrast mediums with different contrast-producing elements, with the elements being selected from the following list: I, La, Ce, Pr, Nd, Sm, Eu, Gd, Tb, Dy, Ho, Er, Tm, Yb, Lu, Bi, for example, from the list: Dy, Ho, Er, Tm, Yb, Lu. One example of this could be a set of contrast mediums with the contrast-producing elements I, Sm and Er. However, in principle, it should be noted that a greater number of different contrast mediums also allows more optimized selection.

Alternatively, and possibly additionally, the contrast mediums available for selection can also be mixed, so that different contrast medium mixtures with different complexes are used. The list of elements used in this case remains the same. However, it is now possible to use appropriate mixture ratios of the contrast mediums for better matching to the current recording situation and therefore to achieve the optimum contrast-to-noise ratio by "fine tuning" the mixture ratios of a small number of contrast mediums. Overall, this allows relatively ideal matching to the recording situation to be achieved despite a smaller number of individual contrast mediums being available.

Mixtures of different contrast mediums in principle conceal the problem that the components may become unmixed prior to being given or in the body. In order to avoid this problem, the inventors propose that contrast mediums be used which have different chemically bonded contrast-forming elements. For example, a contrast medium may have a complex with an La atom and a Gd atom, or two complexes, each having an La and a Gd atom. The mixture ratio is therefore specified such that the mixture ratio cannot change as a result of application problems. For example, fixed mixture ratios of 1:2 of two different elements or 1:1:1 of three different elements can also be achieved by means of three chemically bonded contrast-forming elements. Mixture ratios of 1:3, 2:2, 1:1:2 or 1:1:1:1 may be predetermined as appropriate when using four chemically bonded contrast-forming elements. The complexes used may also in this case be selected from the following list: I, La, Ce, Pr, Nd, Sm, Eu, Gd, Tb, Dy, Ho, Er, Tm, Yb, Lu, Bi.

On the basis of the statements made above, it is also within the scope of this invention to use a complex containing lanthanoid in order to produce a contrast medium to assist diagnosis in CT examination in which a combination such as this of a lanthanoid complex for the contrast medium and an energy spectrum of the X-ray radiation used which produces the maximum contrast-to-noise ratio in a CT representation, is selected as a function of the cross section and the tissue structure of the examination area. Reference is made to the various embodiments of this use as mentioned above.

With regard to the chemical composition, reference is made, for example, to international patent application WO 2004/074267 A1 and to European patent EP 0 222 886 B1, whose disclosure content is included in its entirety with regard to the production of contrast mediums. However, the MR agents Multihance®, Porhance®, Omniscan®, Magnevist® (DE 33 02 410), Primovist®, Gadovist® or Vasovist® which have already been licensed for MRI examinations are also suitable for this purpose. Furthermore, the metal complexes based on the teaching in patent specification U.S. Pat. No. 5,746,995 or mixtures of a metal complex and contrast medium containing iodine according to patent application US 2005/0053551 A1 may also be used.

BRIEF DESCRIPTION OF THE DRAWINGS

Example embodiments of the invention will be explained in more detail in the following text with reference to the drawings, in which:

FIG. 5 shows simulation values of the contrast-to-noise ratio for various contrast mediums with different contrast-forming elements with respect to water using two acceleration voltages, in each case with and without filter hardening;

FIG. 6 shows simulation values from FIG. 5 as mass equivalents, normalized with respect to the dose for the same contrast-to-noise ratio of the contrast medium;

DETAILED DESCRIPTION OF THE EXAMPLE EMBODIMENTS

Embodiments will be described in more detail in the following text with reference to the figures, which illustrate only those features which are necessary for understanding of the invention. The following reference symbols are used in this case: 1: CT system; 2: first X-ray tube; 3: first detector; 4: second X-ray tube; 5: second detector; 6: gantry housing; 7: patient; 8: patient couch; 9: system axis; 10: control and computation unit; 11: memory; 12: contrast medium applicator; 13: time contrast profile; 14: aorta abdominalis; Prgx: computer programs.

The basic design of the CT system according to an embodiment of the invention may, for example, comprise a conventional CT system with a single focus/detector system, with the X-ray tube that is used having at least the capability to influence the energy spectrum of the X-ray radiation that is used. This may be done, for example, by controlling the acceleration voltage or by insertion of filters into the beam path. Systems such as these are generally known. The selection means, which will be described in more detail later are, of course, additionally integrated in the CT system according to embodiments of the invention, as an additional component. In this context, it should be noted that in principle any known CT system which has the capability to influence the energy spectrum used for the X-ray radiation or bremsstrahlung may be adapted according to the invention.

Figure 1:
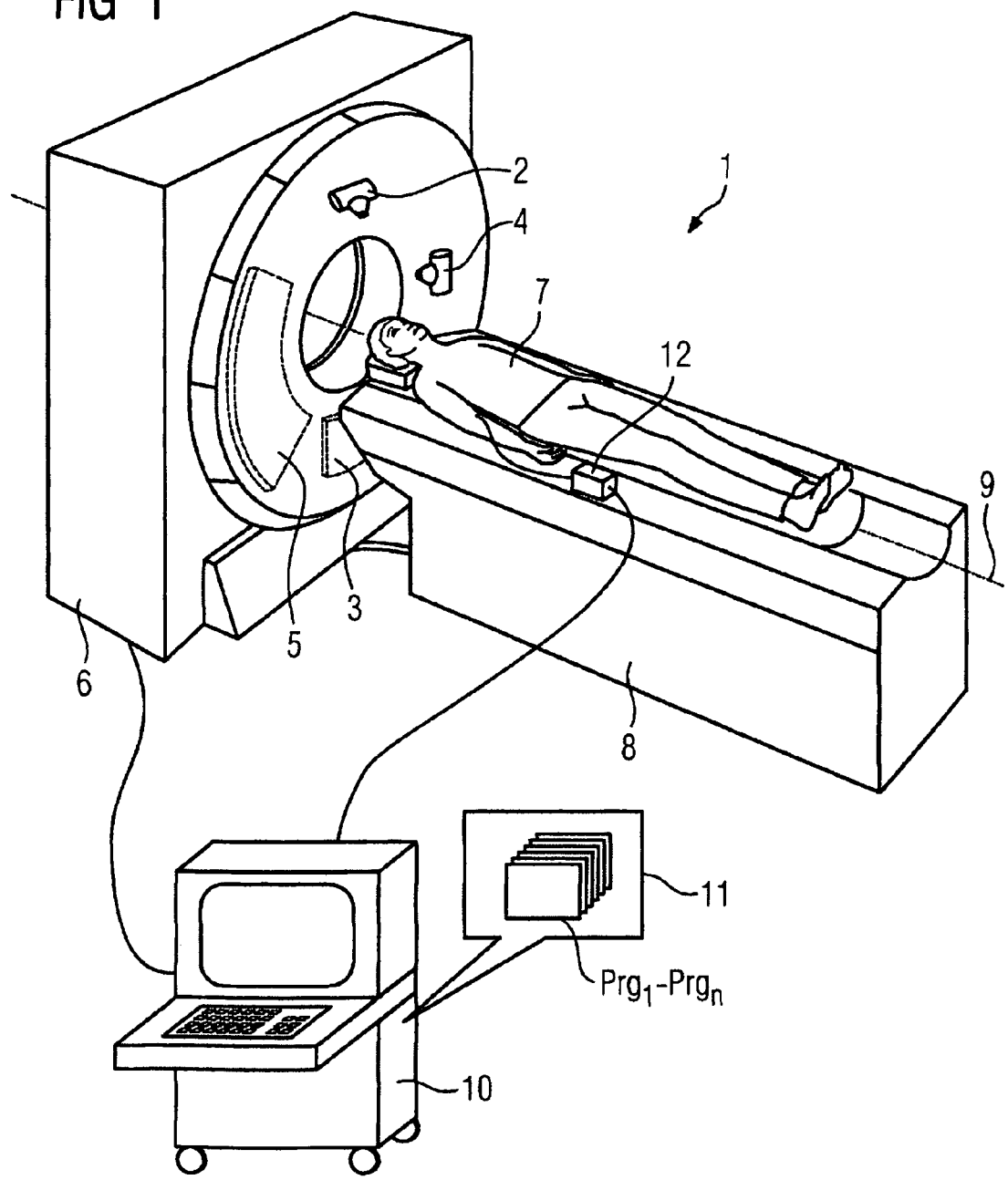
FIG. 1 shows a CT system with a contrast medium injector.

By way of example, a double- or multiple-focus/detector system 1 may also be used, as illustrated in FIG. 1. A CT system 1 such this has a first X-ray tube 2 with an opposite detector 3, and a second X-ray tube 4 with a further opposite detector 5. The two focus/detector systems 2, 3 and 4, 5 are arranged in a gantry housing 6 on a gantry, which rotates about a system axis 9, that is not illustrated in a visible form here. The patient 7 is located on a patient couch 8 which can be moved longitudinally and is passed continuously or in steps through an opening in the gantry housing 6, while the focus/detector systems are being rotated in order to scan the patient 7. This results in the patient 7 being scanned in a spiral shape, or in a number of circles.

Before the patient 7 is scanned, a contrast medium is applied to the patient 7 to improve the contrast of a CT representation reconstructed from the detector output data.

This may be done, for example, by means of a contrast medium injector 12 which injects the selected contrast medium at a given or predetermined flow rate, possibly also varied over time, into the patient 7.

For a cardiac examination, by way of example, the contrast medium may be designed such that it remains exclusively in the blood circulation after being injected, before being dissipated. This allows the blood vessels to be displayed very well, and allows appropriate clinical evaluation. However, it is also possible to use a contrast medium which is specifically attached to a tumor tissue and correspondingly enhances it, as a tumor marker. This results in this tumor being highly enhanced in the CT examination, therefore making it easy to diagnose its position and extent. By way of example, combinations of the two variants described above are also possible, in which case different contrast-forming elements then can preferably be used and can be represented separately on the basis of their different energy-specific absorption behaviours.

A control and computation unit 10 can carry out the control of the entire CT system 1 and possibly also the evaluation of the detector data and reconstruction of the CT representations as slice images or volume data. This control and computation unit 10 has a memory 11 in which not only the measured detector output data but also computer programs Prg1-Prgn are stored which are run during operation and essentially control the system and evaluate the data.

It should be noted that the selection means, selection device or selector according to at least this embodiment of a CT is in the form of a computer program Prgx in the control and computation unit 10. The required inputs to the selector, such as the patient diameter or examination region, can be made via the keyboard. The outputs from the selector to the operator in the form of the optimum contrast medium/radiation combination to be selected can be provided via the screen. Alternatively, this combination can also be passed on within the computer, and can be included directly in the control process.

Furthermore, in this context, it should be noted that it is also within the scope of the invention for the CT system to be connected to a plurality of computer systems, and for individual computation steps to be carried out locally in other computation units.

The use of a double- or multiple-focus/detector system as shown in FIG. 1 offers various advantages over a conventional CT system. For example, two or more different detectors with different operating modes may be used if no detectors are available which can be switched to different operating modes, while being of the same design. In addition, a prescan or the actual scan can be carried out at the same time with each focus/detector system, in each case using a different energy spectrum. Simple simultaneous recording of a plurality of tomograms is likewise possible in order to determine the patient dimensions, thus simplifying subsequent optimum selection of the correct contrast medium/radiation combination.

The basic principle of embodiments of the invention are illustrated in the graphs in the following FIGS. 2 to 12.

Figure 2:
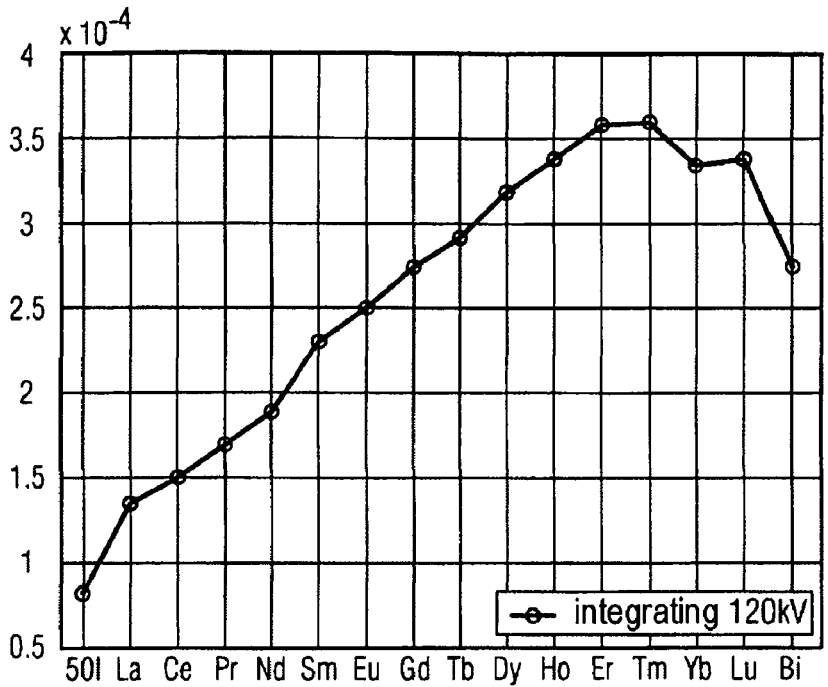
FIG. 2 shows simulation valves of the contrast-to-noise ratio of various contrast mediums with different contrast-forming elements with respect to water with 120 kV X-ray radiation.

FIG. 2 shows simulation values of the contrast-to-noise ratio CNR2/dose, plotted on the abscissa, and normalized with respect to the dose for the various contrast mediums with the contrast-producing elements I (=iodine), La (=lanthanum), Ce (=cerium), Pr (=praseodymium), Nd (=neodymium), Sm (=samarium), Eu (=europium), Gd (=gadolinium), Td (=terbium), Dy (=dysprosium), Ho=(holmium), Er (=erbium), Tm (=thulium), Yb (=ytterbium), Lu (=lutetium), Bi (bismuth) with respect to water with an X-ray radiation of 120 kV are plotted on the ordinate. In this case an energy-integrating detector of the normal type at that time was simulated as the detector.

A cylindrical phantom composed of water with an internally concentrically arranged, considerably smaller cylinder filled with contrast medium was simulated for this simulation. The contrast-to-noise ratios illustrated in the figures correspond to the contrast-to-noise ratio originating from the image reconstructed in this way.

The contrast-producing elements in this FIG. 2 are plotted from left to right with rising atomic number. The results show that, as the atomic number rises, an improvement is initially evident in the form of an increase in the contrast-to-noise ratio. A small plateau of the contrast-to-noise ratio is reached with the contrast-forming elements Er and Tm, followed by a discontinuous drop in the contrast-to-noise ratio to Bi.

Figure 3:
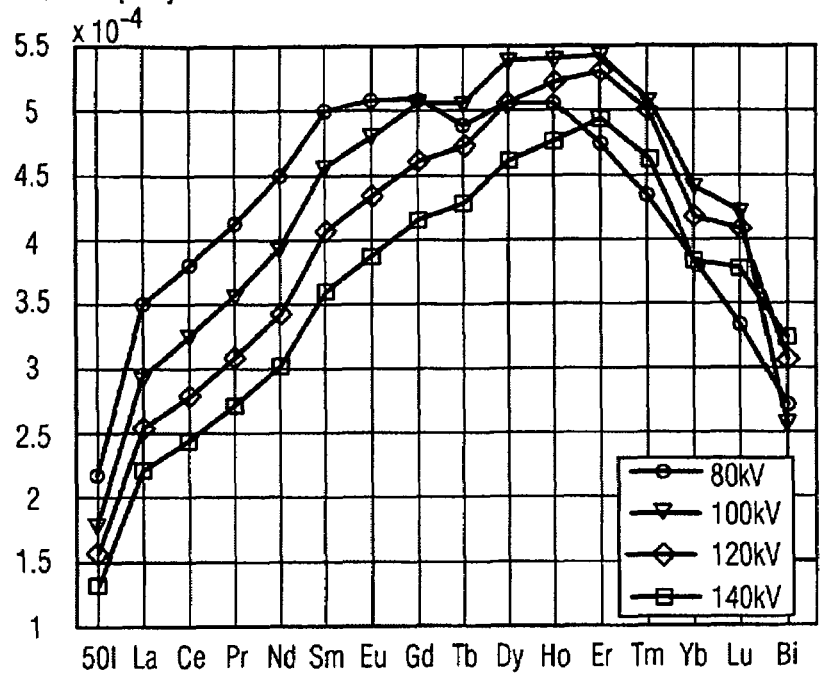
FIG. 3 shows simulation values of the contrast-to-noise ratio of various contrast mediums with different contrast-forming elements with respect to water with unfiltered X-ray radiation using a different acceleration voltage.

If this contrast-to-noise ratio is plotted for spectrally different X-ray beams produced by different acceleration voltages, then it becomes evident that a shift in the energy spectra of these radiations also results in a shift in the contrast-to-noise ratios, in particular in a shift in the curve maxima. In FIG. 3, the simulation values of the contrast-to-noise ratio for various contrast mediums with different elements are plotted with respect to water with unfiltered X-ray radiation and with a different acceleration voltage. In this case, scan results were simulated with X-ray beams from acceleration voltages of 80, 100, 120 and 140 kV, and with the contrast-to-noise ratio CNR2/dose being plotted against the contrast-forming elements with a rising atomic number. Analysis of the results shows that, on the one hand, as the acceleration voltage increases, the maximum of the contrast-to-noise ratio has a tendency to be shifted towards higher atomic numbers. At the same time, the maximum of the contrast-to-noise ratio—ignoring the contrast medium used—occurs at the bremsstrahlung of 100 keV. The shift in the energy spectrum towards higher values leads to a poorer achievable contrast-to-noise ratio. However, if the contrast-forming elements from 1 to Gd are considered, then a continuous increase can be observed in the contrast-to-noise ratio as the acceleration voltage falls. However, this system breaks down for higher atomic numbers.

For example, the elements Tb to Bi produce a contrast-to-noise ratio maximum valve at an acceleration voltage of 100 kV, while the minimum value for Tb to Ho is produced with 140 kV radiation, that for Er to Lu is produced by 80 kV radiation and that for Bi is produced by 100 kV radiation.

Figure 4:
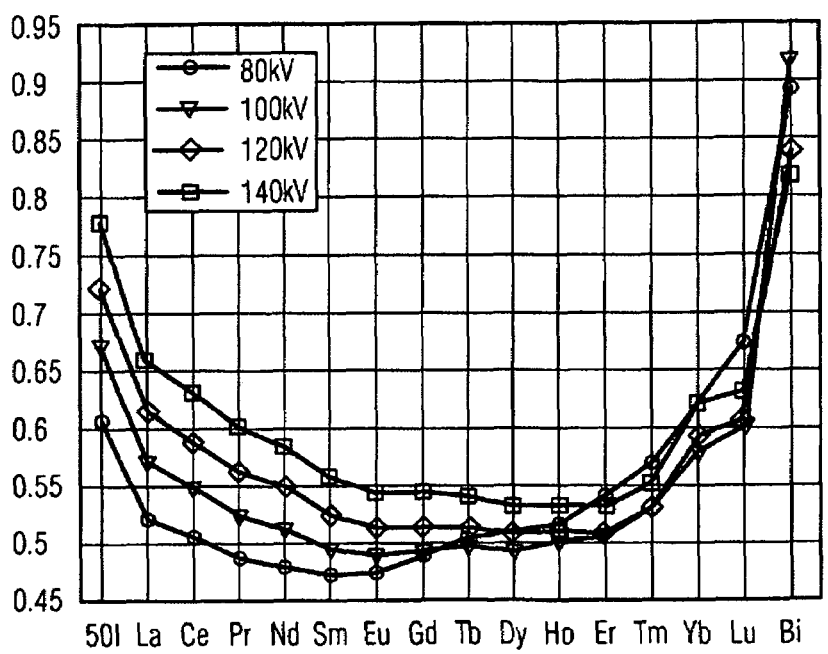
FIG. 4 shows simulation values from FIG. 3 as mass equivalents, normalized with respect to the dose for the same contrast-to-noise ratio of the contrast medium.

FIG. 4 shows these simulation values from FIG. 3 once again plotted as mass equivalents, normalized with respect to the dose, for the same contrast-to-noise ratio with respect to the elements. Fundamentally, this is effectively renormalization of the curves from FIG. 3. These curves indicate that, for example, in the area from 1 to Sm, the use of lower acceleration voltages and of contrast-forming elements with a higher atomic number leads to a reduction in the required contrast medium concentration for the same contrast-to-noise ratio. However, this statement is no longer valid as the atomic number increases further.

Overall, even the knowledge gained from FIGS. 3 and 4 leads to a relatively complex problem when the aim is to find an optimum combination of contrast medium and X-ray radiation using simple rules.

This problem is further exacerbated if the analysis is also intended to take account of shifts in the energy spectra of useable X-ray radiation by means of filters inserted in the beam path.

FIG. 5 shows the simulation values of the contrast-to-noise ratio for various contrast mediums with different elements with respect to water using the two acceleration voltages 80 kV and 120 kV, in each case with and without beam hardening by copper filters. In this case as well there is a major shift in the maxima of the achievable contrast-to-noise ratio, with the influence of the filtering being greater for the 80 kV radiation than for the 120 kV radiation. Since the same filter thickness was used for both radiation levels, the effect of beam hardening was also relatively greater for the 80 kV radiation than for the 120 kV radiation.

Figure 7:
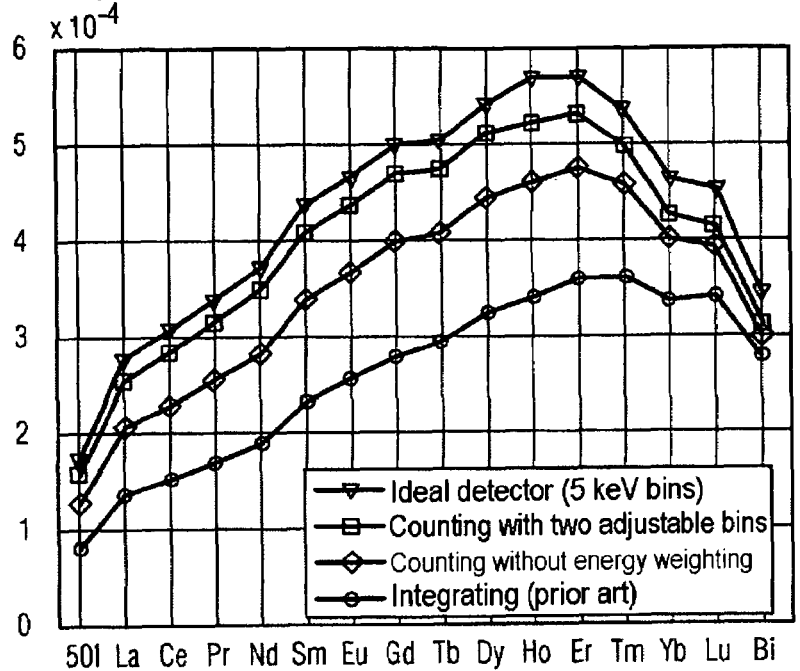
FIG. 7 shows simulation values of the contrast-to-noise ratios for various contrast mediums with different contrast-forming elements with respect to water with X-ray radiation for four different detectors.

In FIG. 6, the simulation values from FIG. 5 are once again plotted as mass equivalents, normalized with respect to the dose, for the same contrast-to-noise ratio for various contrast mediums. A further effect which influences the behavior of the contrast-to-noise ratios of different contrast mediums with respect to one another with different radiation is the operating mode of the detector that is used. FIG. 7 shows the simulation values of the contrast-to-noise ratio of various contrast mediums with different contrast-forming elements with respect to water with X-ray radiation for four different detectors with different operating modes. In this case, results are compared using a simple energy-integrating detector, an event-counting detector, a detector which counts events on an energy-specific basis with two energy ranges and a detector which counts events on an energy-specific basis with energy ranges with a 5 keV interval. The shift which can be observed here in the maxima of the detected contrast-to-noise ratios falls away less severely, but it is evident that the contrast-to-noise ratio can be drastically improved by the use of more specific detectors, with a clear shift in the maximum between the simple integrating detector and the more specific event-counting detectors.

Figure 8:
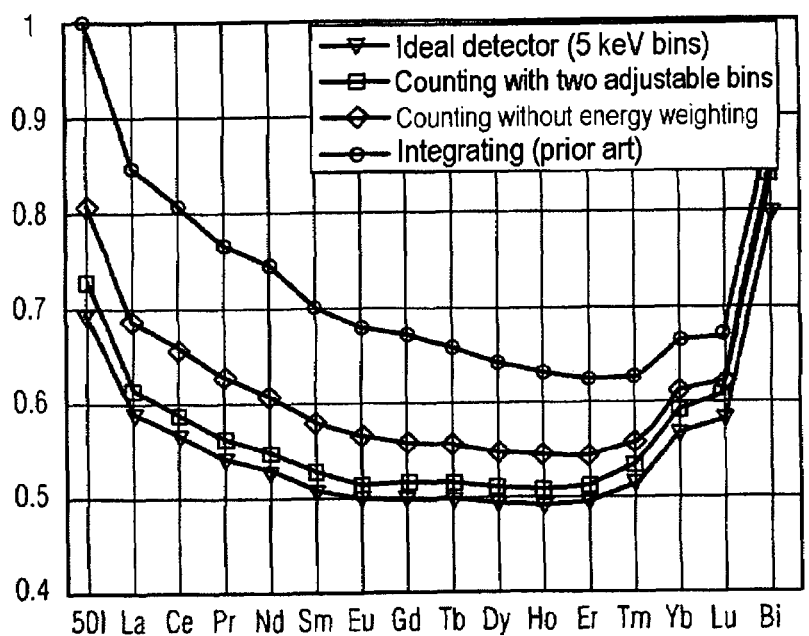
FIG. 8 shows simulation values from FIG. 7 as mass equivalents normalized with respect to the dose for the same contrast-to-noise ratio of the contrast medium.

As before, in this case as well in FIG. 8 below, the same simulation values from FIG. 7 are once again plotted as mass equivalents, normalized with respect to the dose, for the same contrast-to-noise ratio for various contrast mediums.

A considerably more significant problem for the selection of the correct contrast medium/radiation combination is represented by the dimensions of the scanned object and the position of the examined region under consideration. The beam hardening which occurs as the X-ray radiation passes through a patient results in significant shifts with respect to the optimum selection of a contrast medium, depending on the thickness of a patient.

Figure 9:
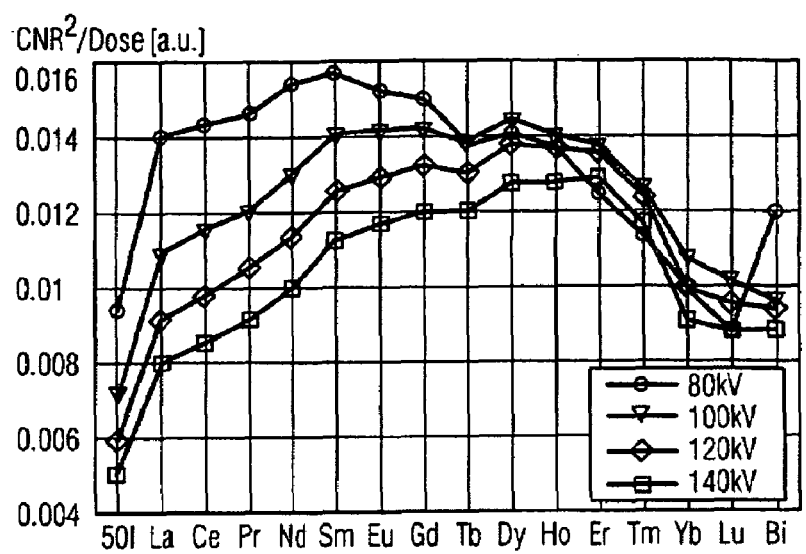
FIG. 9 shows simulation values as shown in FIG. 3 with a cylindrical phantom with a diameter of 20 cm.
Figure 10:
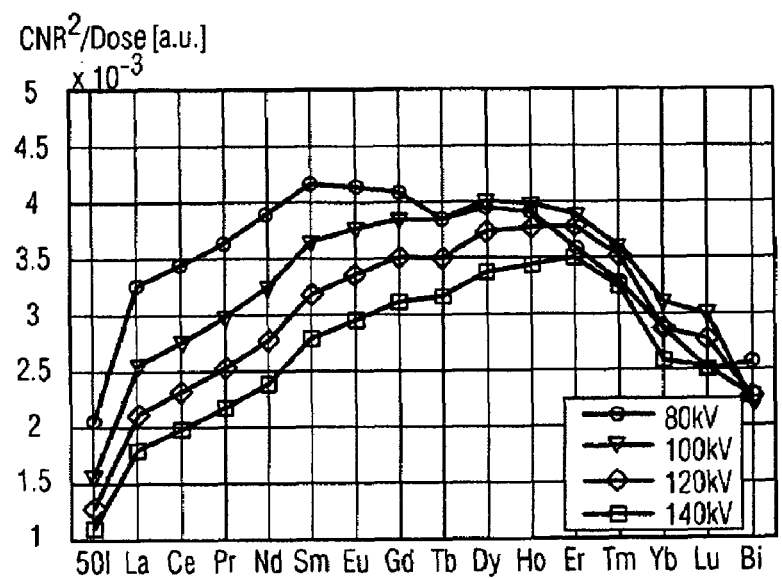
FIG. 10 shows simulation values as shown in FIG. 3 with a cylindrical phantom with a diameter of 30 cm.
Figure 11:
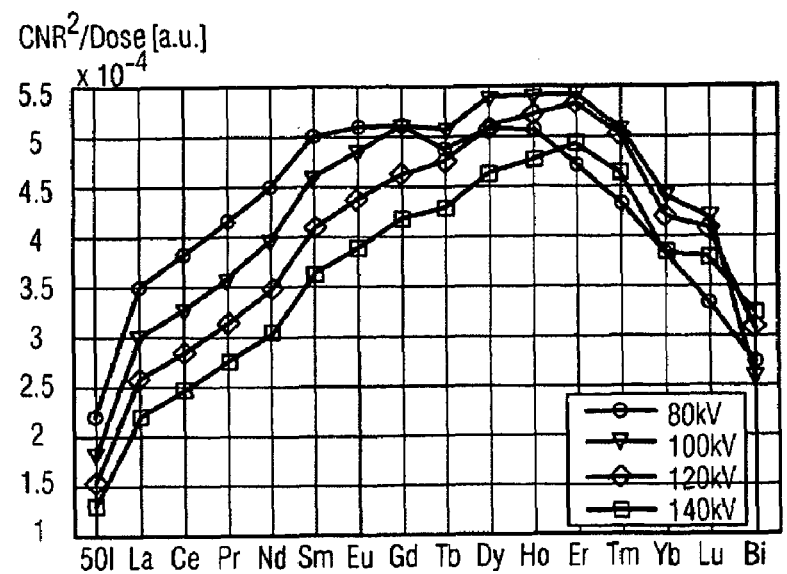
FIG. 11 shows simulation values as shown in FIG. 3 with a cylindrical phantom with a diameter of 40 cm.

In order to illustrate this situation, FIGS. 9 to 11 show the simulation values corresponding to FIG. 3 with a cylindrical phantom with diameters of 20 cm, 30 cm and 40 cm, with a small cylinder filled with contrast medium being arranged centrally in the phantom. These FIGS. 9 and 10 show the simulation results for in each case four different X-ray radiations with acceleration voltages of 80, 100, 120 and 140 kV. In this case, FIG. 11 corresponds identically to FIG. 3.

It is self-evident that it is better for selection of an optimum contrast medium for small diameters of 20 cm and 30 cm to carry out a CT scan for the combination of 80 kV radiation using contrast medium containing Sm while, with the conditions otherwise being the same, the use of Dy, Ho or Er with 100 kV radiation is preferable for a phantom diameter of 40 cm.

The examples described above have illustrated simulations with contrast medium with only a single metal complex. However, it is also possible to use contrast medium mixtures and in this way to achieve further improved matching.

Figure 12:
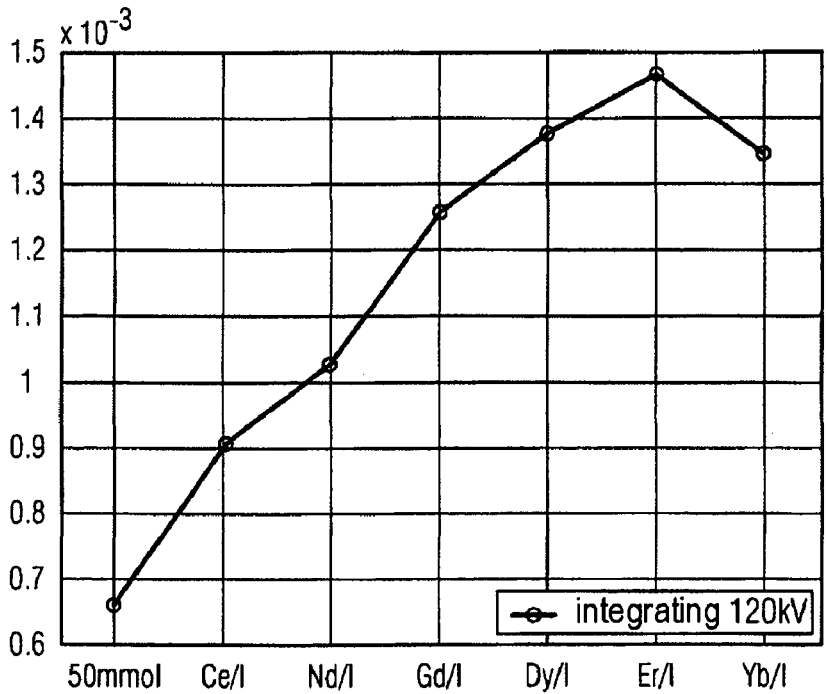
FIG. 12 shows simulation values of the contrast-to-noise ratio for various contrast medium mixtures with different contrast-forming elements and the same basic component with respect to water with X-ray radiation at 120 kV.

FIG. 12 shows simulation values such as these for the contrast-to-noise ratio of the various contrast medium mixtures with different contrast-producing elements and iodine with respect to water using 120 kV X-ray radiation.

It should be noted that the illustrated results are simulation results, although they can also be equivalently replaced by direct measurements. Furthermore, all of the illustrated results have been determined with respect to a water environment. If the aim is to determine a further improved selection and matching of the contrast mediums and their combination with radiation variants and detector variants, it would be better to record these measured values with respect to actual tissue structures since further distinguishing actions are possible as well on the basis of different environments for the contrast medium.

In addition, experimental examinations on animals have been carried out in order to compare the contrast medium component gadolinium with the aid of the contrast medium Gadovist® and the contrast medium component iodine with the aid of the contrast medium Ultravist®.

Methods:
CT Siemens Somaton Volume Zoom 80, 120 and 140 kV tube voltage; of the same tube current in mAs; range 150-300 mAs.
Reconstruction slice thickness: 6 mm.
Protocol perfusion body from the dome of diaphragm to the pelvic symphysis.

Substances Used:
ZK 35760 Ultravist® 300 (300 mg I/ml) commercially available
ZK 135079 Gadovist® (1.0 mol Gd/l) commercially available Dose and Application Protocol:
G1: Ultravist 300 mg I/kg CM
G2: Gadovist 1 mol Gd/kg CM (157 mg Gd/kg CM)
G3: Gadovist 2 mol Gd/kg CM (314 mg Gd/kg CM)
G4: Gadovist estimate how much is required in order to achieve the same ΔHU in the vessels, in this case the aorta.
80, 120 and 140 kV used in each case for all items G1 to G4.
Animals: Dog, n=12; human; anesthetic Rompun®+Ketavet® 1:2; 1 ml/kg CM) average.

Treatment Plan/Procedure:
The measurement protocol is intended to allow angiography of the major chest vessels (aorta, cava, v. portae) and generation of a kidney representation (human protocol: standard abdomen). The animals are scanned with high resolution for 8 minutes.

Desired Evaluation:
The ΔHU values were determined equivalent to the HU values minus the baseline value in the chest vessels and the kidneys for different tube voltages. The radiation dose to be applied was calculated up for the established protocol. Finally, the dosage reduction which the use of gadolinium would allow for the same image quality was estimated.

Figure 13:
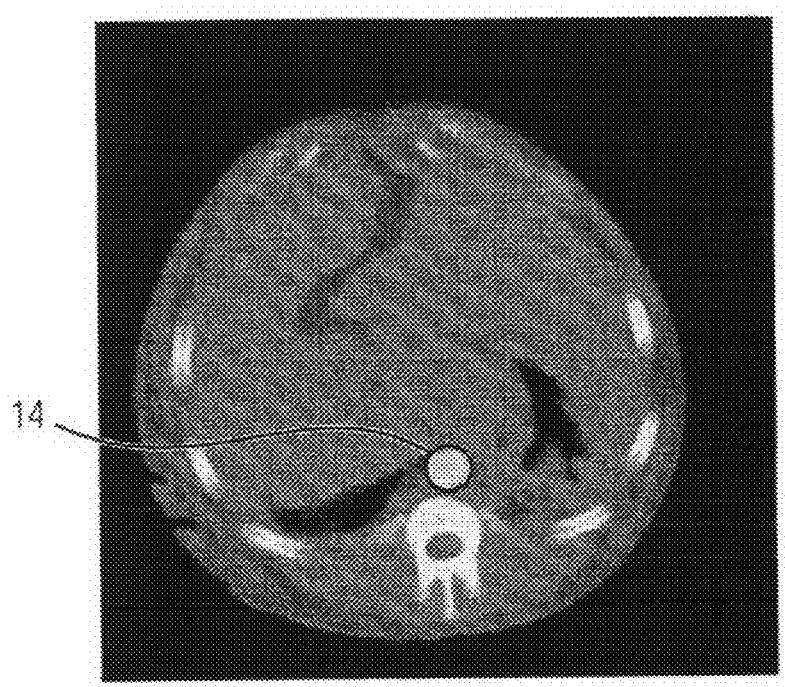
FIG. 13 shows a slice recording of a dog using the contrast medium Gadovist.
Figure 14:
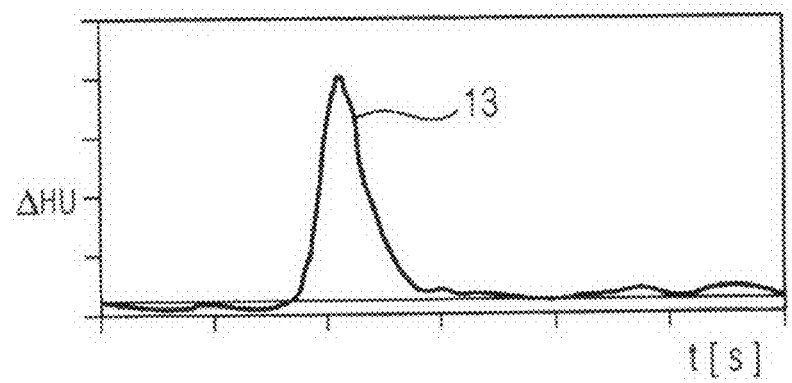
FIG. 14 shows the time profile of the ΔHU values in the aorta from FIG. 13.

Result:
FIG. 13 illustrates an example of a scan record. The time profile 13 of the ΔHU value of the contrast medium bolus in the detailed area illustrated (=aorta abdominalis) 14 is illustrated in FIG. 14.

Figure 15:
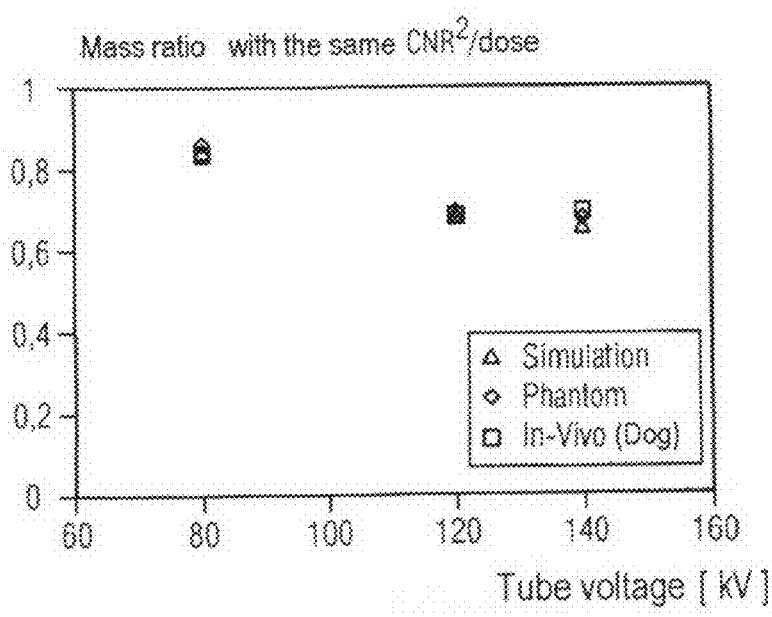
FIG. 15 shows mass equivalents, normalized with respect to the dose for the same contrast-to-noise ratio with respect to the tube voltage in the aorta abdominales.

The measured values for gadolinium and iodine correspond to in-vivo parallel simulation data and phantom experiments. A comparison is provided in FIG. 15. In this case, the mass equivalents, normalized with respect to the dose, are shown for the same contrast-to-noise ratio with respect to three different tube voltages of 80, 120 and 140 kV from simulation results, phantom experiments and the 14 in-vivo examinations in FIGS. 13 and 14. With a tube voltage of 140 kV, 0.68 mg of gadolinium gave the same CT contrast as 1 mg of iodine.

Using the example of gadolinium, it was possible to show in-vivo that lanthanoids achieve greater CT contrast than iodine for clinically relevant tube voltages.

It is self-evident that the features of the invention mentioned above, can be used not only in the respectively stated combination but also in other combinations or on their own, without departing from the scope of the invention.

Therefore, in summary, this invention proposes a CT system having a selector for the best combination of contrast medium and energy spectrum of X-ray radiation used for scanning, in order to optimize the noise-to-contrast ratio, a method for production of CT representations with the aid of contrast mediums and taking account of an optimum combination of contrast medium and energy spectrum of the X-ray radiation used for scanning, and the use of a complex containing lanthanoid in order to produce a contrast medium for optimization of the combination of contrast medium and radiation in order to achieve the maximum contrast-to-noise ratio in a CT representation.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. An X-ray system for creating diagnostic representations of a patient, the X-ray system being capable of selecting different operating parameters at least with respect to the energy spectrum used for the X-ray radiation, the X-ray system comprising:
   an X-ray tube to produce a beam composed of X-rays with an energy spectrum to scan the patient;
   a detector to measure attenuation of the X-ray radiation passing through the patient;
   an application unit to provide contrast medium, the contrast medium providing contrast in the X-ray representation of the patient;
   a control and computation unit to control the X-ray system and create the X-ray representations of the patient with the aid of stored and executed computer programs; and
   a selection means which, after direct or indirect statement of the parameters, presets at least one combination of contrast medium and energy spectrum of the X-ray radiation for the examination, by means of which an optimum contrast-to-noise ratio is achieved in the examination area, the parameters including at least examination volume and tissue structure.

2. The X-ray system as claimed in claim 1, wherein the selection means comprises: a look-up table to store optimum combinations of contrast medium and the energy spectrum of the X-ray radiation
   as a function of the body region to be examined or the tissue structure to be examined.

3. The X-ray system of claim 1, wherein the selection means is connected to a control system for the tube voltage, the control system controlling the tube voltage in accordance with the selection made by the operator.

4. The X-ray system as claimed in claim 1, wherein the selection means is connected to a control system for at least one filter, the filter being insertable into the beam path of the X-ray radiation to vary the energy spectrum of the radiation, the control system controlling the at least one filter in accordance with the selection made by the operator.

5. The X-ray system as claimed in claim 1, wherein an event-counting detector is provided as the detector.

6. The X-ray system as claimed in claim 1, wherein the detector is an energy-selective detector.

7. The X-ray system as claimed in claim 6, wherein the detector detects at least two energy ranges separately, with the at least one limit value between the detected energy ranges being variable, and the selection means is connected to a control system for this limit value, and this limit value is set on an optimized basis, corresponding to the existing presets and the selection made by the operator.

8. The X-ray system as claimed in claim 6, wherein the detector detects at least two energy ranges separately on an event-counting basis, with the at least one limit value between the detected energy ranges being variable and with the selection means being connected to a control system for this limit value, and with this limit value being set on an optimized basis, corresponding to the existing presets and the selection made by the operator.

9. The X-ray system as claimed in claim 1, wherein an indirect input capability is provided for the examination volume by definition of the body region.

10. The X-ray system as claimed in claim 1, wherein the X-ray system is a transillumination system for creating transmission records.

11. The X-ray system as claimed in claim 1, wherein the X-ray system is a CT system or a C-arc system having means for reconstructing tomographic slice or volume representations.

12. The X-ray system as claimed in claim 9, wherein the examination volume is defined by a prescan and is transferred automatically.

13. The X-ray system as claimed in claim 11, wherein the examination volume is defined by recording a topogram and is transferred automatically.

14. The X-ray system as claimed in claim 9, wherein the examination volume is defined optically and is transferred automatically.

15. The X-ray system as claimed in claim 9, wherein the examination volume is defined by a weight definition, the weight definition being obtained by means of a weighing apparatus in the patient couch, and being transferred automatically.

16. The X-ray system as claimed in claim 1, wherein each of the contrast mediums available in the selection means contain at least one of I, La, Ce, Pr, Nd, Sm, Eu, Gd, Tb, Dy, Ho, Er, Tm, Yb, Lu, Bi.

17. The X-ray system as claimed in claim 1, wherein the contrast medium which is available in the selection means has at least one complex and, as a contrast-forming element, contains at least two of I, La, Ce, Pr, Nd, Sm, Eu, Gd, Tb, Dy, Ho, Er, Tm, Yb, Lu, Bi.

18. The X-ray system as claimed in claim 17, wherein at least one contrast medium includes Dy, Ho, Er, Tm, Yb, Lu.

19. A method for optimizing X-ray representations of a patient, the method comprising:
   determining, prior to examination, a contrast-to-noise ratio of different energy spectra of X-ray radiation and different contrast mediums relative to tissue or to material similar to tissue; and selecting, prior to examination of a patient by the X-ray system, at least one contrast medium/X-ray spectrum combination on the basis of a given examination area of the patient.

20. The method as claimed in claim 19, wherein a look-up table is used for selection, in which at least one optimum combination of contrast medium to energy spectrum of the X-ray radiation to be used is stored as a function of the predetermined examination area of the patient.

21. The method as claimed in claim 19, wherein, after a prescan of the examination area, an optimum combination of contrast medium and energy spectrum of the X-ray radiation used for scanning is determined on the basis of actual absorption values in the examination area by simulation using different available contrast mediums and energy spectra.

22. The method as claimed in claim 21, wherein the prescan is carried out using different energy spectra.

23. The method as claimed in claim 21, wherein the prescan is carried out using detectors with different operating modes for dose definition.

24. The method as claimed in claim 19, wherein, after the selection of the contrast medium, which is initiated by the operator, the tube voltage is set automatically in accordance with previously stored details.

25. The method as claimed in claim 19, wherein, after the selection of the contrast medium, which is initiated by the operator, the energy spectrum of the X-ray radiation used in accordance with previously stored details is set automatically by filtering.

26. The method as claimed in claim 19, wherein radiation events are counted in order to determine the absorption of the radiation in the detector.

27. The method as claimed in claim 19, wherein the radiation arriving at the detector is detected on an energy-specific basis in order to determine the absorption.

28. The method as claimed in claim 27, wherein at least two energy ranges are detected separately, but in each case integrated, with the at least one limit value between the detected energy ranges being variably adjustable, and with this limit value being controlled in accordance with the selection made by the operator and existing presets as a function of the contrast medium used and the energy spectrum of the X-ray radiation.

29. The method as claimed in claim 27, wherein at least two energy ranges are detected separately and with events being counted, with the at least one limit value between the detected energy ranges being variably adjustable, and with this limit value being controlled in accordance with the selection made by the operator and existing presets as a function of the contrast medium used and the energy spectrum of the X-ray radiation.

30. The method as claimed in claim 19, wherein, a measure for the volume of the patient to be examined is also entered for selection of the optimum combination of contrast medium and energy spectrum, and a look-up table is used which takes account of this patient volume for the selection process.

31. The method as claimed in claim 30, wherein the patient volume is determined by a prescan and is transferred, preferably automatically.

32. The method as claimed in claim 30, wherein the patient volume is determined by recording a topogram and is transferred, preferably automatically.

33. The method as claimed in claim 30, wherein the patient volume is determined optically and is transferred, preferably automatically.

34. The method as claimed in claim 30, wherein the patient volume is determined by a weight determination, preferably by means of a weighing apparatus in the patient couch, and is transferred, preferably automatically.

35. The method as claimed in claim 19, wherein at least two different contrast mediums are provided for selection and each have at least one contrast-forming element from the following list: I, La, Ce, Pr, Nd, Sm, Eu, Gd, Tb, Dy, Ho, Er, Tm, Yb, Lu, Bi.

36. The method as claimed in claim 35, wherein at least one contrast medium is provided for selection and has a contrast-forming element from the following list: Dy, Ho, Er, Tm, Yb, Lu.

37. The method as claimed in claim 35, wherein at least one contrast medium comprising a mixture of individual components with two different contrast-forming elements is provided for selection.

38. The method as claimed in claim 35, wherein at least one contrast medium has a chemical bond to at least two different contrast-forming elements.

39. An X-ray system including program modules configured to execute computer-executable instructions, which when executed carry out the method of claim 19.

40. A computer readable medium having computer-executable instructions for performing a method according to claim 19.

41. A method for diagnosis assistance in an X-ray examination using a complex containing lanthanoid to produce a contrast medium, the method comprising:
selecting a combination of a lanthanoid complex for the contrast medium and an energy spectrum of the X-ray radiation to produce a maximum contrast-to-noise ratio in an X-ray representation, the selecting being performed as a function of a cross section and tissue structure of examination area.

42. The method as claimed in claim 41, wherein the complex containing lanthanoid of a molecule contains at least one of La, Ce, Pr, Nd, Sm, Eu, Gd, Tb, Dy, Ho, Er, Tm, Yb or Lu.

43. The method as claimed in claim 42, wherein the complex containing lanthanoid also contains at least one of iodine and bismuth.

44. The method as claimed in claim 41, wherein the complex of a molecule containing lanthanoid at the same time contains at least two of La, Ce, Pr, Nd, Sm, Eu, Gd, Tb, Dy, Ho, Er, Tm, Yb or Lu.

45. The method as claimed in claim 44, wherein the complex containing lanthanoid also contains at least one of iodine and bismuth together.

* * * * *